(12) United States Patent
Yin et al.

(10) Patent No.: US 8,729,237 B1
(45) Date of Patent: May 20, 2014

(54) POLYPEPTIDE ADJUVANT COMPOSITION WITH THERMOSTABILITY AND MANUFACTURE THEREOF

(71) Applicant: National Tsing Hua University, Hsinchu (TW)

(72) Inventors: Hsien-Sheng Yin, Hsinchu (TW); Chao-Sheng Cheng, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 0 days.

(21) Appl. No.: 13/745,086

(22) Filed: Jan. 18, 2013

(30) Foreign Application Priority Data

Nov. 9, 2012 (TW) .............................. 101141785 A

(51) Int. Cl.
*C07K 14/03* (2006.01)
(52) U.S. Cl.
USPC .......................................... 530/351; 530/402
(58) Field of Classification Search
None
See application file for complete search history.

(56) References Cited

U.S. PATENT DOCUMENTS

2009/0005266 A1* 1/2009 Ostermeier et al. ............ 506/17

OTHER PUBLICATIONS

Hung et al (Vaccine. Feb. 3, 2010;28(5):1148-55. Epub Nov. 28, 2009).*

* cited by examiner

*Primary Examiner* — Brian J Gangle
*Assistant Examiner* — Andrea McCollum
(74) *Attorney, Agent, or Firm* — WPAT, P.C.; Anthony King; Kay Yang

(57) ABSTRACT

The present invention provides a polypeptide adjuvant composition with thermostability, which is designed from wild-type chicken interleikin-1β to construct a new chicken interleikin-1β, named CP-interleikin-1β. The CP-interleikin-1β having improved heat resistance keeps the original biological activity, and which helps to develop protein adjuvant with high efficiency and uses in medical application. The present invention also provides a method of manufacturing such polypeptide adjuvant composition.

5 Claims, 11 Drawing Sheets

SEQUENCE LISTING

<160> NUMBER OF SEQ ID NOS: 12

<210> SEQ ID NO 1
<211> LENGTH: 381
<212> TYPE: DNA
<213> ORGANISM: chicken
<220> FEATURE:
<223> OTHER INFORMATION: Interleukin-1

<400> SEQUENCE: 1

```
caggggccct cctccagcca gaaagtgagg ctcaacattg cgctgtaccg gccccgaggc    60
ccacggggca gcgctggaac tgggcagatg ccagtggcac tgggcatcaa gggctacaag   120
ctctacatgt cgtgtgtgat gagcggcacc gagcccacac tgcagctgga ggaagccgac   180
gtcatgcggg acatcgacag cgtcgagctg acccgcttca tcttctaccg cctggacagc   240
ccgactgagg gcaccacgcg cttcgagtcg gccgccttcc ccgggtggtt catctgcacc   300
tccctgcagc cccggcagcc cgtgggcatc accaaccaac ccgaccaggt caacatcgcc   360
acctacaagc taagtgggcg c                                             381
```

<210> SEQ ID NO 2
<211> LENGTH: 105
<212> TYPE: DNA
<213> ORGANISM: chicken
<220> FEATURE:
<223> OTHER INFORMATION: Interleukin-1

<400> SEQUENCE: 2

```
gcgcccgcct ccgctacac ccgctcacag tccttcgaca tcttcgacat caaccagaag    60
tgcttcgtgc tggagtcacc cacccagctg gtggccctgc acctc                   105
```

<210> SEQ ID NO 3
<211> LENGTH: 78
<212> TYPE: DNA
<213> ORGANISM: Artificial Sequence
<220> FEATURE:
<223> OTHER INFORMATION: Linker Sequence

<400> SEQUENCE: 3

```
ggtaccggtg gttcaggtgg ttcaggtggt tcaggtggtt caggtggctc tggtggctct    60
ggtggttcag gtggatcc                                                  78
```

<210> SEQ ID NO 4
<211> LENGTH: 26
<212> TYPE: PRT
<213> ORGANISM: Artificial Sequence
<220> FEATURE:
<223> OTHER INFORMATION: Linker Sequence

<400> SEQUENCE: 4

Gly Thr Gly Gly Ser Gly Gly Ser Gly Gly Ser Gly Gly Ser Gly Gly Ser Gly
1               5                   10                  15

Gly Ser Gly Gly Ser Gly Gly Ser
        20                  25

<210> SEQ ID NO 5
<211> LENGTH: 30
<212> TYPE: DNA
<213> ORGANISM: Artificial Sequence
<220> FEATURE:
<223> OTHER INFORMATION: Forward primer of WT chicken IL-1

```
<400> SEQUENCE: 5
cgaagcttgc gcccgccttc cgctacaccc                                    30

<210> SEQ ID NO 6
<211> LENGTH: 32
<212> TYPE: DNA
<213> ORGANISM: Artificial Sequence
<220> FEATURE:
<223> OTHER INFORMATION: Reverse primer of WT chicken IL-1

<400> SEQUENCE: 6
cgggatccgc gcccacttag cttgtaggtg gc                                 32

<210> SEQ ID NO 7
<211> LENGTH: 36
<212> TYPE: DNA
<213> ORGANISM: Artificial Sequence
<220> FEATURE:
<223> OTHER INFORMATION: Forward primer of the nucleotide linker
      sequence

<400> SEQUENCE: 7
acctgaacca ccggtaccgc gcccacttag cttgta                             36

<210> SEQ ID NO 8
<211> LENGTH: 31
<212> TYPE: DNA
<213> ORGANISM: Artificial Sequence
<220> FEATURE:
<223> OTHER INFORMATION: Reverse primer of the nucleotide linker
      sequence

<400> SEQUENCE: 8
ggtggttcag gtggatccgc gcccgccttc c                                  31

<210> SEQ ID NO 9
<211> LENGTH: 18
<212> TYPE: DNA
<213> ORGANISM: Artificial Sequence
<220> FEATURE:
<223> OTHER INFORMATION: Forward primer of chemokine K60

<400> SEQUENCE: 9
atgatgggca aggctgta                                                 18

<210> SEQ ID NO 10
<211> LENGTH: 18
<212> TYPE: DNA
<213> ORGANISM: Artificial Sequence
<220> FEATURE:
<223> OTHER INFORMATION: Reverse primer of chemokine K60

<400> SEQUENCE: 10
ttaggatgca gtcttatt                                                 18

<210> SEQ ID NO 11
<211> LENGTH: 22
<212> TYPE: DNA
<213> ORGANISM: Artificial Sequence
<220> FEATURE:
<223> OTHER INFORMATION: Forward primer of ?-Actin

<400> SEQUENCE: 11
atgtttgaga ccttcaacac cc                                            22

<210> SEQ ID NO 12
```

-continued

```
<211> LENGTH: 23
<212> TYPE: DNA
<213> ORGANISM: Artificial Sequence
<220> FEATURE:
<223> OTHER INFORMATION: Reverse primer of ?-Actin

<400> SEQUENCE: 12
atgtcacgca caatttctct ctc                                      23
```

POLYPEPTIDE ADJUVANT COMPOSITION WITH THERMOSTABILITY AND MANUFACTURE THEREOF

CROSS-REFERENCE TO RELATED APPLICATIONS

This application claims the priority benefit of Taiwan application serial no. 101141785, filed on 9 Nov. 2012. The disclosure of the Taiwan application is incorporated by reference herein.

BACKGROUND OF THE INVENTION

1. Field of the Invention

The present invention relates to a polypeptide adjuvant composition, and in particular, to a polypeptide adjuvant composition with thermostability.

2. The Prior Arts

In March and April 1997, there were outbreaks of H5N1 avian influenza viruses on several poultry farms in the province of Hong Kong. These viruses were highly pathogenic in chickens and resulted in high mortality of infected chickens. During this same period, the continuing occurrence of infection of humans with influenza virus led to fears of a deadly influenza pandemic. It resulted in huge economic impact and financial crisis. The best way to prevent infection with avian influenza is to avoid sources of exposure whenever possible. Most bird infections with avian influenza in poultry farms will be culled to avoid the viruses spreading. However, in high-density poultry farms, once the high-pathogenic avian influenza outbreaks, the speed of culling the infected birds may be less than that of the high-pathogenic avian influenza spread. Vaccination is the most effective way to prevent infection and severe outcomes caused by influenza viruses. And it needs to step up the preventive measures against avian influenza.

Growth in the veterinary vaccines market is primarily attributed to augmented public awareness and technological innovations. Many newly developed vaccines are considered advantageous over traditional vaccines in terms of production volumes and immune response. Growing demand for the vaccines and increased vulnerability to diseases such as avian influenza, is steering the demand for veterinary vaccines in the emerging Asia-Pacific regions, Moreover, the altering patterns of diseases among animals and increased development of resistance to currently used antimicrobials is compelling manufacturers to invest heavily in new product developments.

For prevention of bird infection with avian influenza viruses, a vaccine with excellent quality may reduce the rate of the birds infected and the viruses transmitted. And it is very important to manufacture vaccine adjuvants which can enhance antigen-specific immune responses. Two main known vaccine adjuvants in livestock are aluminum-based and oil-based. The adverse effect of both vaccine adjuvants is chemical-makeup, wherein the aluminum-based adjuvant can not enhance the specificity of the Th1 cell immune response. Oil-based adjuvant can trigger immune system response, but it may result in local inflammation and granulomatous reactions at the site of injection, chronic inflammation, skin ulceration, local abscess or tissue sloughing, diffuse systemic granulomas, and it is also unable to enhance the production of antibodies.

Recently, the vaccine adjuvant has been improved to low or free oil-based, such as biological adjuvant and protein adjuvant. In the past, it is well known that mammalian interleukin-1β is pro-inflammatory cytokines involved in immune defense against infection. Interleukin-1β is mainly expressed by monocytes and macrophages and is synthesized as a precursor. The mature, bioactive interleukin-1β is produced upon caspase 1-mediated proteolysis of the precursor. The active interleukin-1β is then able to interact with type 1 interleukin-1 receptor and induce the expression of immune-related molecules such as cytokines and chemokines, thus triggering a cascade of immune responses. Therefore, interleukin-1β can be used as a vaccine adjuvant for vaccination to stimulate the secretion of chemotactic cytokine and the production of antibodies.

However, most adjuvants are unstable at about 46° C., and it needs to store at a lower temperature and to maintain the bioactivity of antigen and the good physical properties in the vaccine. However, there are heating steps (the range of 40° C. to 60° C.) in the manufacturing process of the protein adjuvant, and it is difficult to breakthrough the barrier of temperature. In addition, vaccines should be stored at the lower temperature from the time they are manufactured until the time them used. Overheating vaccines can cause obvious problem, as the protein in the vaccine will breakdown (denature) and will not produce the desired immune response. Therefore, it is necessary to manufacture a vaccine adjuvant with thermostability.

Interleukin-1β is mainly as a biological adjuvant, but its instability is limited the application. The present invention provides an improved circular permutation chicken interleukin-1β which is obtained by the combination of structural biology, biological information and genetic engineering. Because there are many protein adjuvants unstable at the temperature above 46° C., and chicken interleukin-1β is also included. The circular permutation chicken interleukin-1β of the present invention has been broken through the barrier which has not been overcome by other technology. Furthermore, the present invention also provides a most suitable condition to manufacture and purify the circular permutation chicken interleukin-1β, which is able to facilitate industrial applications.

SUMMARY OF THE INVENTION

The present invention provides a polypeptide adjuvant composition with thermostability, consisting essentially of a circular permutation chicken interleukin-1β (CP IL-1β) encoded by a first fragment SEQ ID NO:1 and a second fragment SEQ ID NO:2, wherein the first fragment is connected to the second fragment via a linker sequence, the linker sequence is a polynucleotide sequence SEQ ID NO:3 encoding a polypeptide SEQ ID NO:4. CP IL-1β of the present invention has thermotolerance in the range 45° C. to 60° C., and the secondary structure of CP IL-1β has α-helix and β-folding, the ratio of α-helix to β-folding is 1.07:1 to 1.35:1.

One object to this invention is to provide a polypeptide adjuvant composition with thermostability which can be applied in an avian vaccine, including but not limited to an avian vaccine, wherein the chicken vaccine is an avian influenza in chicken.

Another object to this invention is to provide a method of manufacturing a polypeptide adjuvant composition with thermostability, comprising: obtain at least one Circular permutation (CP) site of a chicken interleukin polynucleotide sequence using Circular permutation method, digest the chicken interleukin polynucleotide forming two fragment in CP site, and amplify the two fragments by polymerase chain reaction (PCR), connect the amplified two fragments via a linker sequence, transform into a transformant, wherein the transformant is *Escherichia coli*.; and obtain a circular permutation interleukin from the transformamt, after centrifuging and extracting, detect the bioactivity of circular permutation interleukin with thermostability. Wherein the linker sequence is a polynucleotide SEQ ID NO:3 encoding a polypeptide SEQ ID NO:4, and the thermostability is at 45° C.

The invention provides methods of increasing thermotolerance or thermostability of a polypeptide adjuvant composition, consisting essentially of a circular permutation chicken interleukin-1β encoded by a first fragment SEQ ID NO:1 and a second fragment SEQ ID NO:2, wherein the first fragment is connected to the second fragment via a linker sequence, the linker sequence is a polynucleotide sequence SEQ ID NO:3 encoding a polypeptide SEQ ID NO:4., thereby increasing the thermotolerance or thermostability of the polypeptide adjuvant composition. In one aspect, the polypeptide adjuvant composition specific activity can be thermostable or thermotolerant at a temperature in the range 45° C. to 60° C.

The present invention provides a CP IL-1β using Circular permutation method to improve the interleukin-1β of avian. CP IL-1β is more stable to chemical and heating treatment compared with WT chicken IL-1β, and it facilitate the subsequent processing. CP IL-1β exhibits bioactivities in vitro and in vivo, moreover, CP IL-1β retains its bioactivity after high-temperature treatment, which may allow CP IL-1β to be used in medical, industrial and vaccine applications, such as an avian adjuvant. It can solve the secondary structure changed by heating treatment and reduce the cost of the temperature controlled transport or store for the vaccine.

The detailed technology and above preferred embodiments implemented for the present invention are described in the following paragraphs accompanying the appended drawings for one skilled in the art to well appreciate the features of the claimed invention.

DETAILED DESCRIPTION OF THE PREFERRED EMBODIMENT

The present invention provides a circular permutation interleukin-1β (CP IL1β) using Circular permutation (CP) method to improve the polypeptide of wild-type chicken interleukin-1β, consisting essentially of a circular permutation chicken interleukin-1β encoded by a first fragment SEQ ID NO:1 and a second fragment SEQ ID NO:2, wherein the first fragment is connected to the second fragment via a linker sequence, the linker sequence is a polynucleotide sequence SEQ ID NO:3 encoding a polypeptide SEQ ID NO:4, and constructing a new recombinant of chicken interleukin-1β, named circular permutation interleukin-1β.

The present invention of a polypeptide adjuvant composition with thermostability is more stable at high temperature compared with wild type (WT) chicken IL-1β and it still retains the structure of protein at 60° C. Moreover, the polypeptide adjuvant composition of the present invention can retain its bioactivity after chemical and heating treatment. It can be used in therapeutic application such as an avian vaccine adjuvant.

EXAMPLE 1

Construct the Circular Permutation of Chicken Interleukin (IL)-1β

Figure 1:
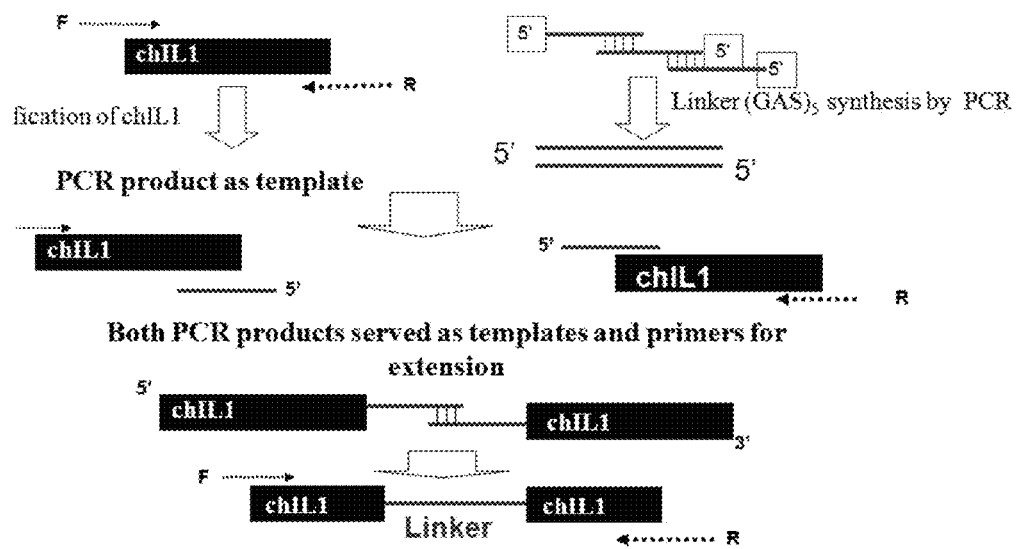
FIG. 1 is a flow chart of constructing a circular permutation interleukin (IL)-1β of the present invention using circular permutation method; chIL1 is the abbreviation of the fragment of wild type (WT) chicken IL-1β.

In one embodiment, the flow chart of constructing the circular permutation interleukin-1β (CP IL-1β) as shown in FIG. 1. Two fragments of wild type (WT) chicken IL-1β is amplified by polymerase chain reaction (PCR) as a starting template. A nucleotide linker sequence SEQ ID NO:3 is obtained by twice PCR that encodes a polypeptide sequence SEQ ID NO:4. The nucleotide linker sequence links the 5' and 3' terminal end of WT chicken IL-1β gene. The gene of wild type (WT) chicken IL-1β with the nucleotide linker sequence is as a template amplified by a forward primer of WT chicken IL-1β gene SEQ ID NO:5 and a reverse primer of the nucleotide linker sequence SEQ ID NO: 8, a reverse primer of WT chicken IL-1β gene SEQ ID NO:6 and a forward primer of the nucleotide linker sequence SEQ ID NO: 7, respectively. Both PCR products serve as templates and primers for extension to obtain an extension production. Final, the extension productions amplified by PCR using forward primer of WT chicken IL-1β gene SEQ ID NO:5 and reverse primer of WT chicken IL-1β gene SEQ ID NO:6 to obtain a final product. The final product having two wild-type chicken polynucleotide fragments and a linker sequence SEQ ID NO:3 are cloned into vector pGEMT (Promega, Wis., U.S.A.).

In addition, two fragments of wild type (WT) chicken IL-1β as a starting template is using circular permutation method (Taiwan patent I356,103) to estimate a CP site of chicken interleukin polynucleotide. A circular permutation interleukin-1β is generated, which is based on the CP site. To increase the accuracy of the CP site is to estimate a temperature factor (B-factor) of protein crystal structure at the same time. The B-factor is indicated the atoms in the crystal fixed or not, the higher values of the crystallographic B-factor imply greater uncertainty in atom positions. After digesting the CP site, two fragments of wild type (WT) chicken IL-1β is generated, a first fragment SEQ ID NO:1 and a second fragment SEQ ID NO:2. Primers for the PCR amplifications are designed with nucleoside sequences appropriate for the new N- and C-terminal end. The circular permutation genes are individually cloned into vector pET-28a(+) (Promega, Wis., USA), with a His6 and T7 tag at the Nterminus The gene sequences are confirmed by DNA sequencing.

Two fragments of wild type (WT) chicken IL-1β is amplified by polymerase chain reaction (PCR) as a starting template, and a nucleotide linker sequence SEQ ID NO:3 links the first fragment and the second fragment to construct a circular permutation interleukin-1β (CP IL-1β). CP IL-1β is cloned into vector pET-28a(+) (Promega, Wis., USA) to produce and purify protein.

EXAMPLE 2

Circular Permutation IL-1β Expression and Purification 2.1 Circular Permutation IL-1β Expression

*Escherichia coli* BL21(DE3) CODONPLUS cells (Stratagene, Amsterdam, The Netherlands) bearing pET-28a(+) containing a gene for the circular permutation IL-1β mutant are cultured in 500 mL of LB broth, 50 μg/mL ampicillin at 37° C. Isopropyl β-D-1-thiogalactopyranoside (final concentration, 0.4 mM) is added to induce protein expression when the OD600 of each culture reach 0.6. After 20 h of incubation, the cells are harvested by centrifugation (8,000×g for 20 min at 4° C.).

2.2 Circular Permutation IL-1β Purification

Each cell pellet is suspended in 25 mM Tris-HCl, 500 mM NaCl, pH 7.4 and lyses by sonication. Each lysate was centrifuged at 100,000×g for 30 min at 4° C., and the recombinant His-tagged protein is purified using a 100-ml $Co^{2+}$ affinity column (BD Biosciences, Calif.). The column is equilibrated with 25 mM Tris-HCl, 500 mM NaCl, pH 7.9. After loading a protein onto the column, it is eluted in the same buffer that also contains 75 mM imidazole. To remove the imidazole and concentrate the protein, a CENTRICON Plus 20 centrifugal filter device (Millipore, Billerica, Mass.) is used. The final products are characterized by 12% (w/v) SDS-PAGE, and the protein concentrations are determined using Bio-Rad Bradford Protein Assay kit reagents (Bio-Rad, Calif.) with bovine serum albumin as the standard.

Figure 2:
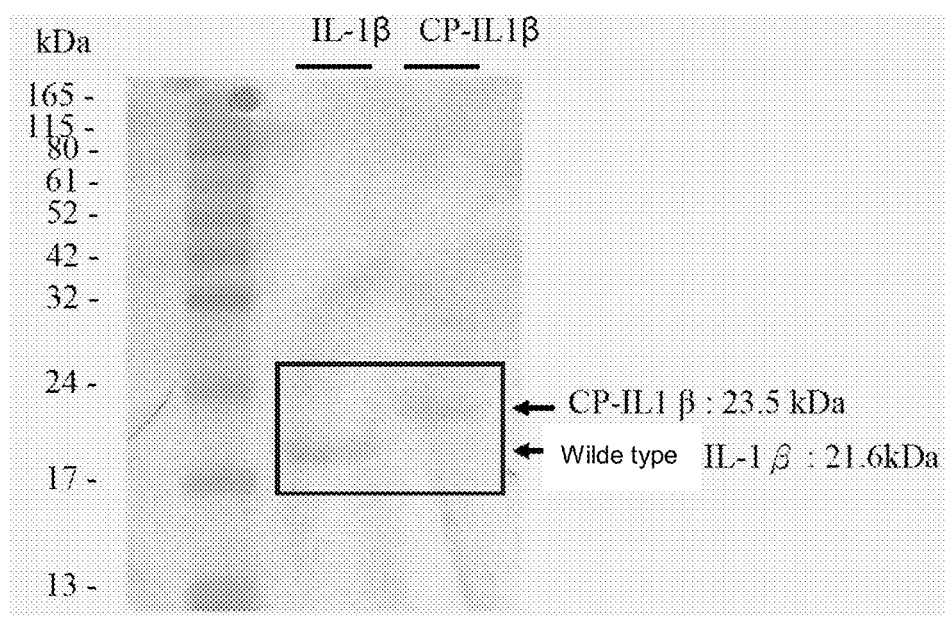
FIG. 2 is 12% sodium dodecyl sulfate polyacrylamide gel electrophoresis (SDS PAGE) of circular permutation interleukin-1β (CP IL-1β) and WT chicken IL-1β after expression and purification.

As shown in FIG. 2, after the WT chicken IL-1β and the circular permutation IL-1β of the present invention express and purify, the molecular weight of WT chicken IL-1β is 21.6 kDa and the molecular weight of the circular permutation IL-1β is 23.5 kDa by 12% sodium dodecyl sulfate polyacrylamide gel electrophoresis (SDS PAGE).

EXAMPLE 3

Determination of Protein Structure

The circular permutation IL-1β (CP IL-1β) of the present invention is obtained by circular permutation, and the structure of CP IL-1β is further determined by circular dichroism (CD) spectroscopy and fluorescence spectrofluorometer.

3.1 Determination of the Circular Permutation IL-1β Secondary Structure

To determine the secondary structure and stability of the circular permutation IL-1β, an Aviv 202 circular dichroism spectropolarimeter (Aviv Biomedical Inc., Lakewood, N.J.) is used to obtain the CD spectra for CP IL-1β and WT chicken IL-1β. For secondary structure characterization, far-UV CD spectra of 10 μM samples in 10 mM potassium phosphate, pH 7.4, are recorded from 260 to 195 nm at 25° C. using a 1-mm path length cuvette. Three CD scans for each sample are averaged and are reported as ellipticity (mdeg).

Figure 3:
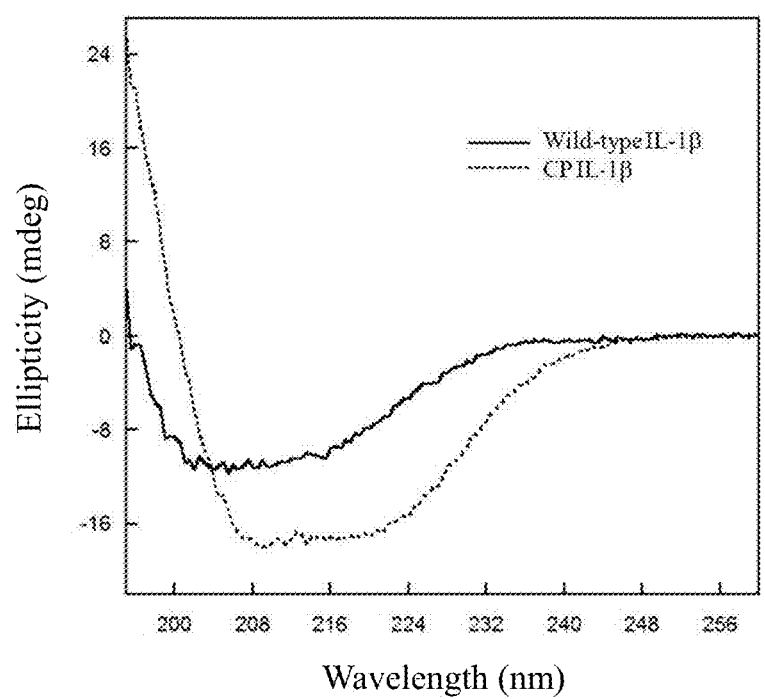
FIG. 3 shows the CD spectra of WT chicken IL-1β and CP IL-1β of the present invention.

In FIG. 3 shows the CD spectra of WT chicken IL-1β at 25° C. A strong signal at 205 nm is indicated more β-folding structure (α-helix is 19.6±1.4% and β-folding is 26.8±1.4%). In contrast, the CD spectra of CP IL-1β has been changed, there is a maximum value at 195 nm and two minimum values at 209 nm and 222 nm. It is indicated the secondary structure of CP IL-1β containing mostly α-helix. The secondary structure of CP IL-1β is included α-helix 26.3±1.6% and β-folding 21.9±1.2% using CDNN software (Applied Photophysics, England).

3.2 Determination of the Circular Permutation IL-1β Folded Structure

The intrinsic fluorescence of 1 mM solutions of CP IL-1β and WT chicken IL-1β each in 25 mM Tris-HCl, 100 mM NaCl, pH 7.4, at 25° C. is measured from 290 nm to 400 nm using an F-7000 fluorescence spectrofluorometer (Hitachi, Tokyo, Japan) and a 1-cm path length cuvette (excitation at 280 nm). To characterize potential interactions between CP IL-1β or WT IL-1β (10 μM each) and the fluorescent hydrophobic dye, 1,8-anilinonaphthalenesulfonate (20 μM), in 25 mM Tris-HCl, 100 mM NaCl, pH 7.4, at 25° C., the fluorescence of the dye is measured from 385 to 600 nm (excitation at 365 nm). Each reported spectrum is the average of three scans and was plotted using KaleidaGraph software (Synergy Software, Reading, Pa., U.S.A.).

Figure 4:
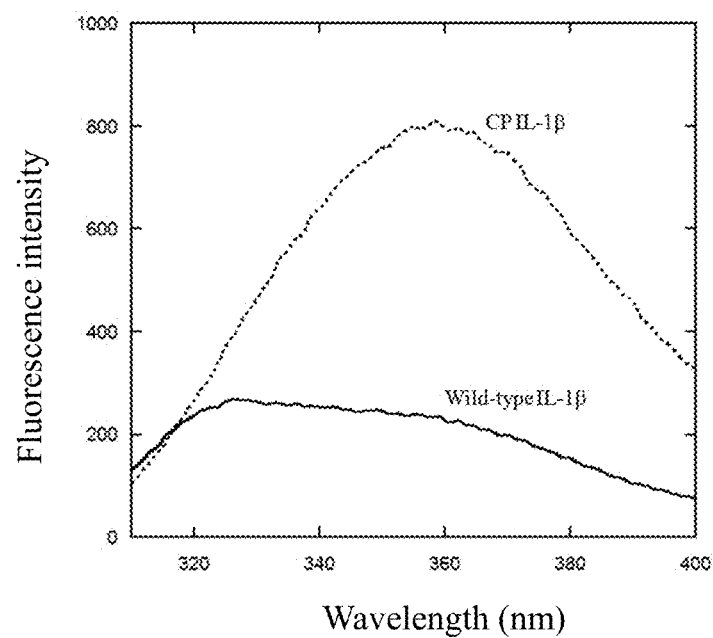
FIG. 4 shows the intrinsic fluorescence of WT chicken IL-1β and CP IL-1β after 1,8-anilinonaphthalenesulfonate (ANS)-binding assay.

FIG. 4 shows the intrinsic fluorescence of WT chicken IL-1β and CP IL-1β after 1,8-anilinonaphthalenesulfonate (ANS)-binding assay. The intrinsic fluorescence of WT chicken IL-1β shows maximum excitation wavelength at 326 nm, implying that aromatic amino acids included tyrosine and tryptophan is embedded in hydrophobic core. In contrast, the intrinsic fluorescence of CP IL-1β shows maximum excitation wavelength at 360 nm, implying that aromatic amino acids is exposed on the surface area of CP IL-1β and not tightly embedded in hydrophobic core. Moreover, fluorescence intensity of both is different, implying that there is different force surrounding aromatic amino acids. Thus, in the present invention, CP IL-1β has folding patterns of the three-dimensional structure different from WT chicken IL-1β.

EXAMPLE 4

Determination of Protein Thermostability and Chemistry Property

The thermostability of CP IL-1β and WT chicken IL-1β is determined at temperatures between 4° C. and 96° C. by recording the changes in the ellipticity (θ) at 217 nm of their CD spectra. The temperature is raised in 2° C. increments at a heating rate of 1° C./min. Prior to recording the ellipticity values, the temperature of the protein sample is equilibrated for 6 sec.

Figure 5A:
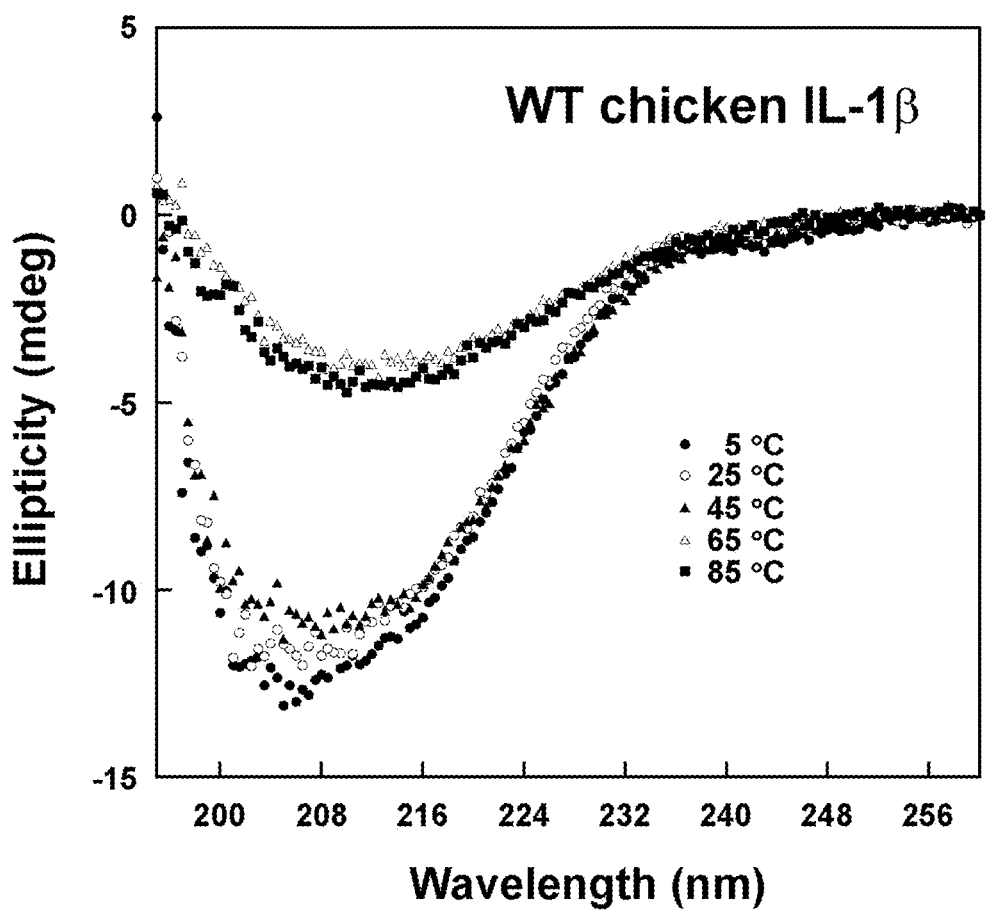
FIG. 5A shows CD spectra of WT chicken IL-1β after heating treatment.
Figure 6:
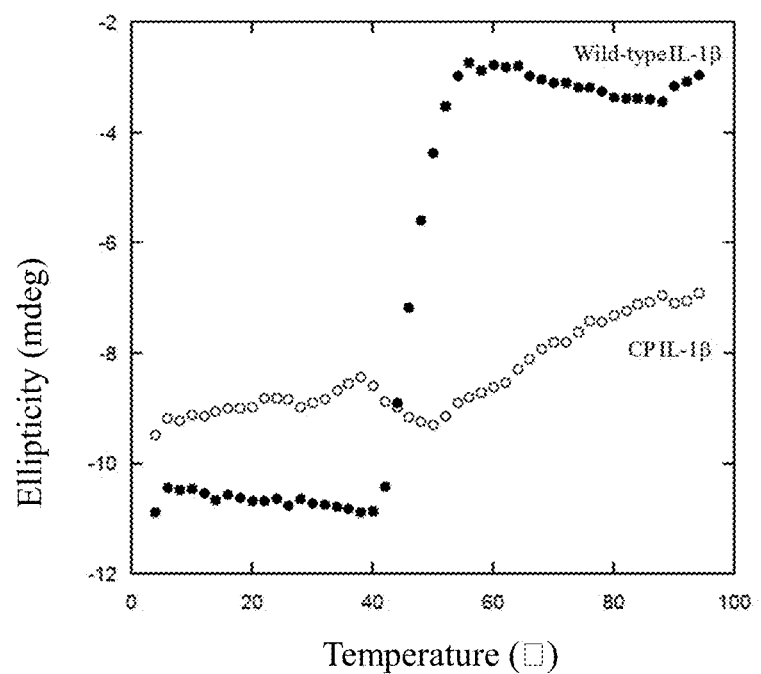
FIG. 6 depicts the thermal denaturation curves of WT chicken IL-1β and CP IL-1β.

FIG. 5A shows the CD spectra of WT chicken IL-1β after heating process to analyses the thermal stability. In the heating process, WT chicken IL-1β has been obviously reduced the ellipticity values. Especially the temperature reaches 65° C., the secondary structure of WT chicken IL-1β has been broken, while the curve shows two states transition model. Refer to the FIG. 6, when the temperature reaching 40° C., the ellipticity values only change slightly. When the temperature over 40° C., the ellipticity values obviously reduce. Where the temperature reaching 56° C., the structure of WT chicken IL-1β expands fully and loses the original structure.

Figure 5B:
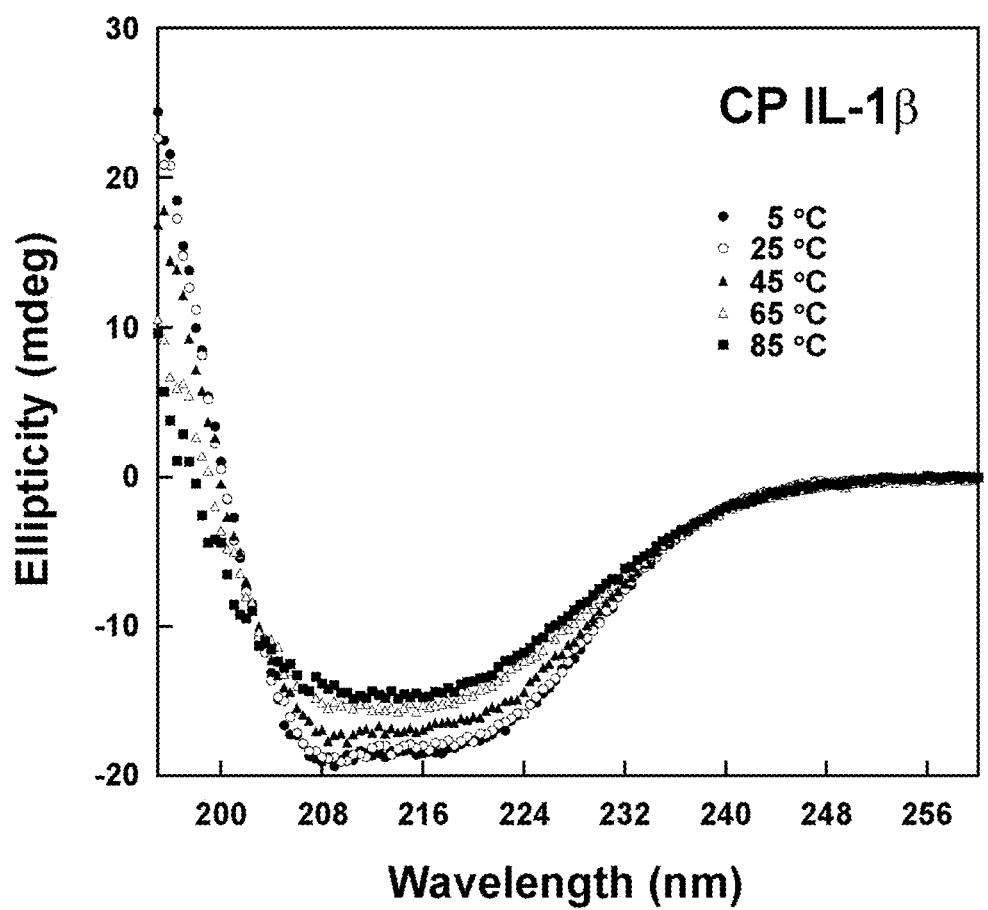
FIG. 5B shows the CD spectra of CP IL-1β after heating treatment.

FIG. 5B shows the CD spectra of CP IL-1β at raised temperature, and CD spectra almost retain the same structure as which at 25° C. Refer to the FIG. 6, when the temperature up to 85° C., the secondary structure of CP IL-1β only has been broken partly. In the experiment, the secondary structure reduced slowly at high temperature (over 60° C.). Accordingly, CP IL-1β of the present invention not only intensifies secondary structure, but also enhances the thermal stability due to the secondary structure and folding pattern of protein changing. CP IL-1β of the present invention can applied broadly and has the benefits of follow-up process and industrial high-throughput.

In addition, the affect of protein folding structure is determined by chemical material. For the guanidine-HCl unfolding experiment, protein samples (10 μM) in 10 mM potassium phosphate, pH 7.4, are mixed with solutions containing various concentrations of guanidine-HCl (GdnHCl) and their ellipticity values are measured at 217 nm, 25° C. Three independent unfolding curves are obtained.

Figure 7:
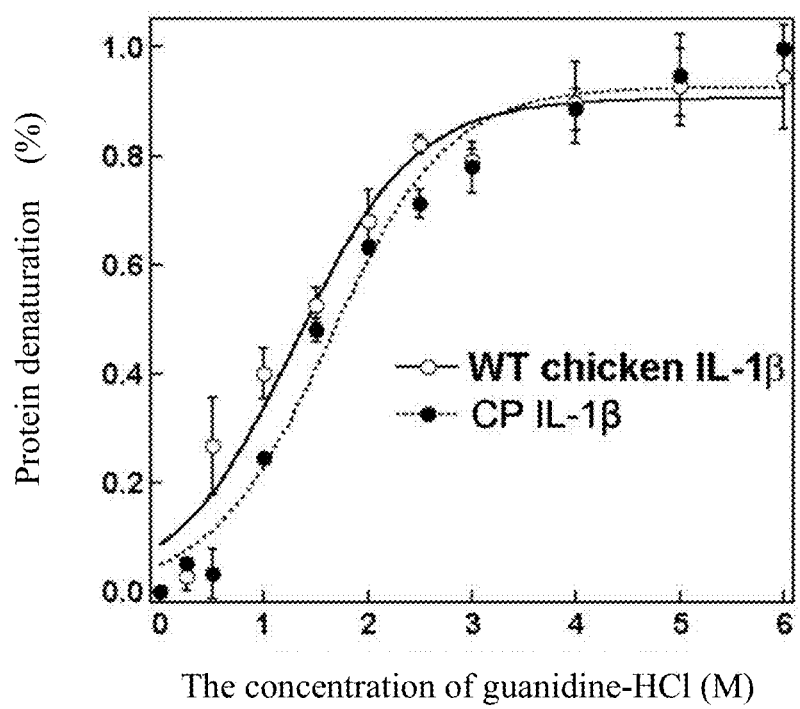
FIG. 7 depicts the chemical (guanidine-HCl) denaturation curves of WT chicken IL-1β and CP IL-1β.

As sown in FIG. 7, protein unfolding is monitored at different guanidine-HCl concentrations by following the change in ellipticity at 217 nm, The fraction unfolded is calculated as $f=(\theta-\theta_F)/(\theta_U-\theta_F)$, where θ is the observed ellipticity at 217 nm, at a given guanidine-HCl concentration, and $\theta_U$ and $\theta_F$ are ellipticities of the denatured and native states, respectively. At 1.4M guanidine-HCl, 50% WT chicken IL-1β gets denatured. At 1.7 M guanidine-HCl, 50% CP IL-1β of the present invention gets denatured. In addition, at 0 to 1.0 M guanidine-HCl, CP IL-1β of the present invention gets denatured more slowly than WT chicken IL-1β. Thus, CP IL-1β of the present invention also enhances greater resistance to chemical denaturants.

EXAMPLE 5

Bioactivity Assay In Vitro

To characterize the bioactivity of CP IL-1β, the mRNA expression level of the pro-inflammatory chemokine K60 in chicken fibroblasts is determined First, chicken DF-1 fibroblasts (from Dr. Lee, Long-Huw at National Chung Hsing University Department of veterinary medicine) are cultured in Dulbecco minimum essential medium (DMEM) supplemented with 4% (v/v) fetal calf serum. CP IL-1β, WT chicken IL-1β and WT human IL-1β (100 ng/ml each) are then individually added into a culture and incubated for 2 h. The K60 mRNA levels were then detected as the measure of bioactivity using RT-PCR kit reagents (SUPERSCRIPT III One-Step RT PCR System, Invitrogen, USA). β-actin mRNA levels served as the internal control. The PCR primer sequences of RT PCR are as following: the forward primer SEQ ID NO: 9 and the reverse primer SEQ ID NO: 10 to detect the K60 mRNA level, the forward primer SEQ ID NO: 11 and the reverse primer SEQ ID NO:12 to detect β-actin mRNA levels. PCR products were identified after electrophoresis through 1.5% (w/w) agarose gels.

Figure 8:
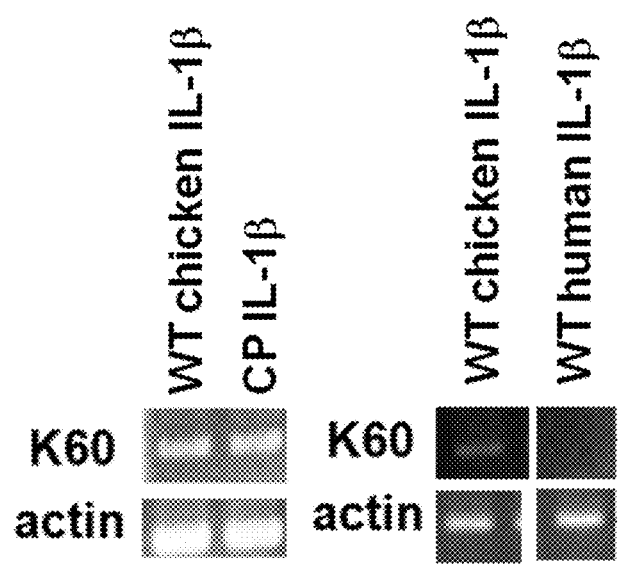
FIG. 8 shows expression levels of chemokine K60 of WT chicken IL-1β and CP IL-1β.

As shown in FIG. 8, the results indicate WT human IL-1β can not promote chemokine K-60 mRNA expression, even through the structure of WT human IL-1β is identical to the structure of WT chicken IL-1β. An obvious agarose-gel band corresponding to K60 mRNA is present in response to CP IL-1β treatment, implying that CP IL-1β, like WT chicken IL-1β, triggers an immune response in fibroblasts. Accordingly, CP IL-1β of the present invention not only enhances the thermostability but also retains the bioactivity as WT chicken IL-1β.

EXAMPLE 6

Bioactivity Assay In Vivo 6.1 Measure Plasma Cortisol Level

To determine the in vivo activity of CP IL-1β, WT chicken IL-1β and WT human IL-1β, each protein is directly injected into the wing vein of adult chickens, after which plasma cortisol level is measured.

CP IL-1β, WT chicken IL-1β and WT human IL-1β are individually injected at a concentration of 10 μg/kg body mass into the wing vein of adult specific-pathogen-free white leghorn chickens (Animal Health Research Institute, Taiwan). The buffer solution (25 mM Tris-HCl, 100 mM NaCl) used to dissolve interleukin-1β serves as the internal control. After 1 h, the plasma cortisol level is measured using a Roche E170 Modular immunoassay analyzer (Roche Diagnostics, Mannheim, Germany).

Figure 9:
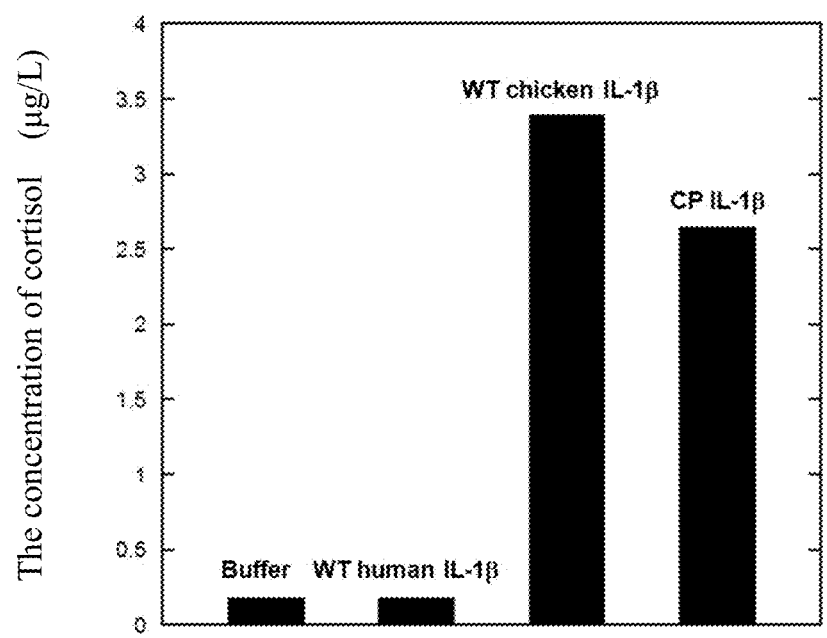
FIG. 9 shows the concentration of plasma cortisol of WT chicken IL-1β, WT human IL-1β and CP IL-1β. The buffer solution used to dissolve interleukin-1β serves as the internal control.

The plasma cortisol level is measured according to Roche E170 Modular immunoassay analyzer protocol. As shown in FIG. 9, the plasma cortisol levels in chickens are significantly enhanced by intravenous injections of WT chicken IL-1β and CP IL-1β, which is not found for human IL-1β. Therefore, CP IL-1β can induce immune and inflammatory responses in chicken, which is consistent with the K60 mRNA assay.

6.2 Measure Plasma Cortisol Level at High Temperature

In addition, to investigate the impact of temperature on the subsequent ability of WT chicken IL-1β or CP IL-1β to increase the plasma cortisol level, solutions of proteins are heat to various temperatures (45° C., 50° C., 55° C., 65° C.) for 10 min and cool to 25° C. They are then immediately injected into chickens; the residual activity is defined as the ratio of the cortisol level after and before the temperature treatment.

The animal-use protocol is reviewed and approved by the Institutional Animal Care and Use Committee (IACUC), National Tsing Hua University, Taiwan. Three independent experiments for each protein that used three chickens are performed.

Figure 10:
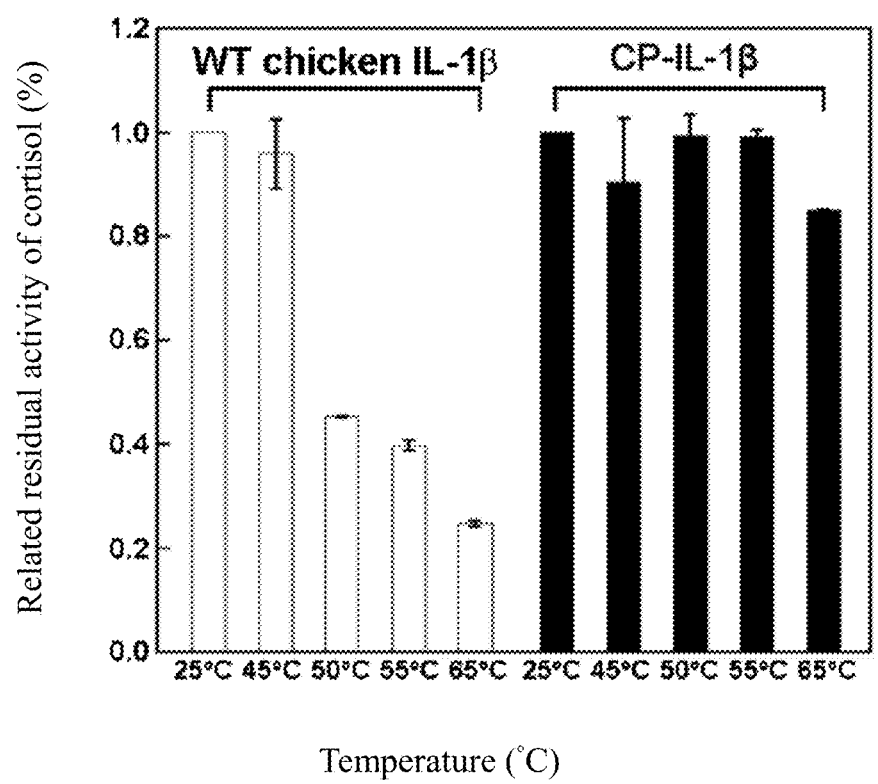
FIG. 10 shows concentration of plasma cortisol of WT chicken IL-1β, WT human IL-1β and CP IL-1β at different temperature (25° C., 45° C., 50° C., 55° C. and 65° C.).

As shown in FIG. 10, solutions of proteins are heat to various temperatures (25° C., 45° C., 50° C., 55° C., 65° C.) and subsequently inject the solution into chickens to measure the serum cortisol level. The results reveal that heated-treated CP IL-1β causes strikingly better immune responses than heat-treated WT chicken IL-β. When heat-treated at 50° C., WT chicken IL-1β looses more than 55% of its activity, and CP IL-1β looses about 1% of its activity. Even after being exposed to 65° C., WT chicken IL-1β looses about 76% of its activity, but CP IL-1β retains more than 80% of its activity. These results demonstrate that the heat tolerance of CP IL-1β allows it to retain its bioactivity, thereby enhancing the vaccine potency.

Therefore, the present invention provides a CP IL-1β which is more stable to chemical and thermal treatments compared with WT chicken IL-1β. CP IL-1β exhibits in vitro and in vivo bioactivities, moreover, CP IL-1β retains its bioactivity after high-temperature treatment, which may allow CP IL-1β to be used in therapeutic application such as an avian vaccine.

What is claimed is:

1. A polypeptide adjuvant composition with thermostability, consisting essentially of a circular permutation chicken interleukin-1β encoded by a first fragment having the sequence of SEQ ID NO:1 and a second fragment having the sequence of SEQ ID NO:2, wherein the first fragment is connected to the second fragment via a linker sequence, the linker sequence is a polynucleotide sequence SEQ ID NO:3 encoding a polypeptide SEQ ID NO:4.

2. The polypeptide adjuvant composition with thermostability according to claim 1, wherein the circular permutation chicken interleukin-1β has thermotolerance in the range 45° C. to 60° C.

3. The polypeptide adjuvant composition with thermostability according to claim 1, wherein the secondary structure of the circular permutation chicken interleukin-1β has α-helix and β-folding, and the α-helix and β-folding has a ratio of a-helix to b-folding of 1:07:1 to 1.35:1.

4. A method of preventing avian disease, comprising administering an avian vaccine to an avian subject, wherein the avian vaccine includes a polypeptide adjuvant composition with thermostability according to claim 1.

5. The method of preventing avian disease of claim 4, wherein the avian vaccine is a chicken vaccine.

* * * * *